United States Patent
Tafti et al.

(10) Patent No.: US 10,667,929 B2
(45) Date of Patent: Jun. 2, 2020

(54) METHOD AND SYSTEM FOR ALIGNING A PROSTHETIC DEVICE

(71) Applicants: Nahid Tafti, Qom (IR); Mohammad Reza Safari Kelayeh, Derby (GB); Mohammad Ali Mardani, Tehran (IR); Amir Salar Jafarpisheh, Tehran (IR); Masoud Karimlou, Tehran (IR); Gholam Reza Aminian, Tehran (IR)

(72) Inventors: Nahid Tafti, Qom (IR); Mohammad Reza Safari Kelayeh, Derby (GB); Mohammad Ali Mardani, Tehran (IR); Amir Salar Jafarpisheh, Tehran (IR); Masoud Karimlou, Tehran (IR); Gholam Reza Aminian, Tehran (IR)

( * ) Notice: Subject to any disclaimer, the term of this patent is extended or adjusted under 35 U.S.C. 154(b) by 137 days.

(21) Appl. No.: 15/889,166

(22) Filed: Feb. 5, 2018

(65) Prior Publication Data

US 2018/0271680 A1 Sep. 27, 2018

(51) Int. Cl.
*A61F 2/76* (2006.01)
*A61F 2/60* (2006.01)
*A61F 2/68* (2006.01)

(52) U.S. Cl.
CPC .......... *A61F 2/76* (2013.01); *A61F 2002/607* (2013.01); *A61F 2002/6881* (2013.01); *A61F 2002/762* (2013.01); *A61F 2002/7625* (2013.01); *A61F 2002/7685* (2013.01)

(58) Field of Classification Search
CPC ...................................................... A61F 2/76
See application file for complete search history.

(56) References Cited

U.S. PATENT DOCUMENTS

| 7,107,832 B2 * | 9/2006 | Blumentritt .......... A61B 5/1036 177/200 |
| 7,594,935 B2 | 9/2009 | Warila |
| 8,452,458 B2 | 5/2013 | Even-Zohar |
| 9,278,014 B2 | 3/2016 | Macomber et al. |

(Continued)

OTHER PUBLICATIONS

Jan W. Raczkowski et al., "Functional scoliosis caused by leg length discrepancy", Arch Med Sci 2010;6(3):393-8.

(Continued)

*Primary Examiner* — Christopher J Beccia
(74) *Attorney, Agent, or Firm* — NovoTechIP International PLLC

(57) ABSTRACT

An improved method of determining prosthetic alignment utilizes a system which includes multiple movable laser units and an integrated scale to measure angles and other variables of an uninjured leg of a patient based on anatomical landmarks, compare those to angles and variables of an amputated side, and make adjustments to a prosthetic device utilized for the amputated side based on the comparison to ensure proper alignment. For example, the amount of tilt to the side of the prosthetic socket, the amount of tilt to the front and back of the prosthetic socket, the amount of tilt of the prosthetic foot on the sagittal plane, the displacement of the prosthetic foot on the sagittal plane, the rotation of the prosthetic foot on the transverse plane, and the height of the prosthetic device can thereby be adjusted based on measured parameters of the uninjured leg to ensure proper alignment.

17 Claims, 20 Drawing Sheets

(56) References Cited

U.S. PATENT DOCUMENTS

2013/0057652 A1* 3/2013 Firth .................. G01B 11/25
348/46
2017/0135608 A1 5/2017 Pappe et al.

OTHER PUBLICATIONS

Julie Kendall et al., "Foot Posture, Leg Length Discrepancy and Low Back Pain—their relationship and clinical management using foot orthoses—An overview", Foot. 2014;24(2):75-80.
W.F. Harvey et al., "Association of le length inequality with prevalent, incident, and progressive knee osteoarthritis: a cohort study", Ann Intern Med. 2010;152(5):287-95.
Terje Terjesen et al., "Leg-length discrepancy measured by ultrasonography", Acta Orthopaedica Scandincavica. 1991;62(2):121-4.
G.R. Clarke, "Unequal leg lenth: an accurate method of detection and some clinical results", Rheumatology. 1972;11(8):385-90.
J.M. Guichet et al., "Lower limb-length discrepancy. An epidemiologic study", Clinical orthopaedics and related research. 1991;272:235-41.
S.I. Subotnick, "Limb length discrepancies of the lower extremity (the short leg syndrome)", Journal of Orthopaedic & Sports Physical Therapy. 1981;3(1):11-6.
A.L. Woerman et al., "Leg Length Discrepancy Assessment: Accuracy and Precision in Five Clinical methods of Evaluation", The journal of orthopaedic and sports physical therapy 1984;5(5):230-9.
N. Tafti et al., "Development and preliminary evaluation of a new anatomically based prosthetic alignment method for below-knee prosthesis", Assistive Technology, The Official Journal of RESNA (2018), 1-28.

\* cited by examiner

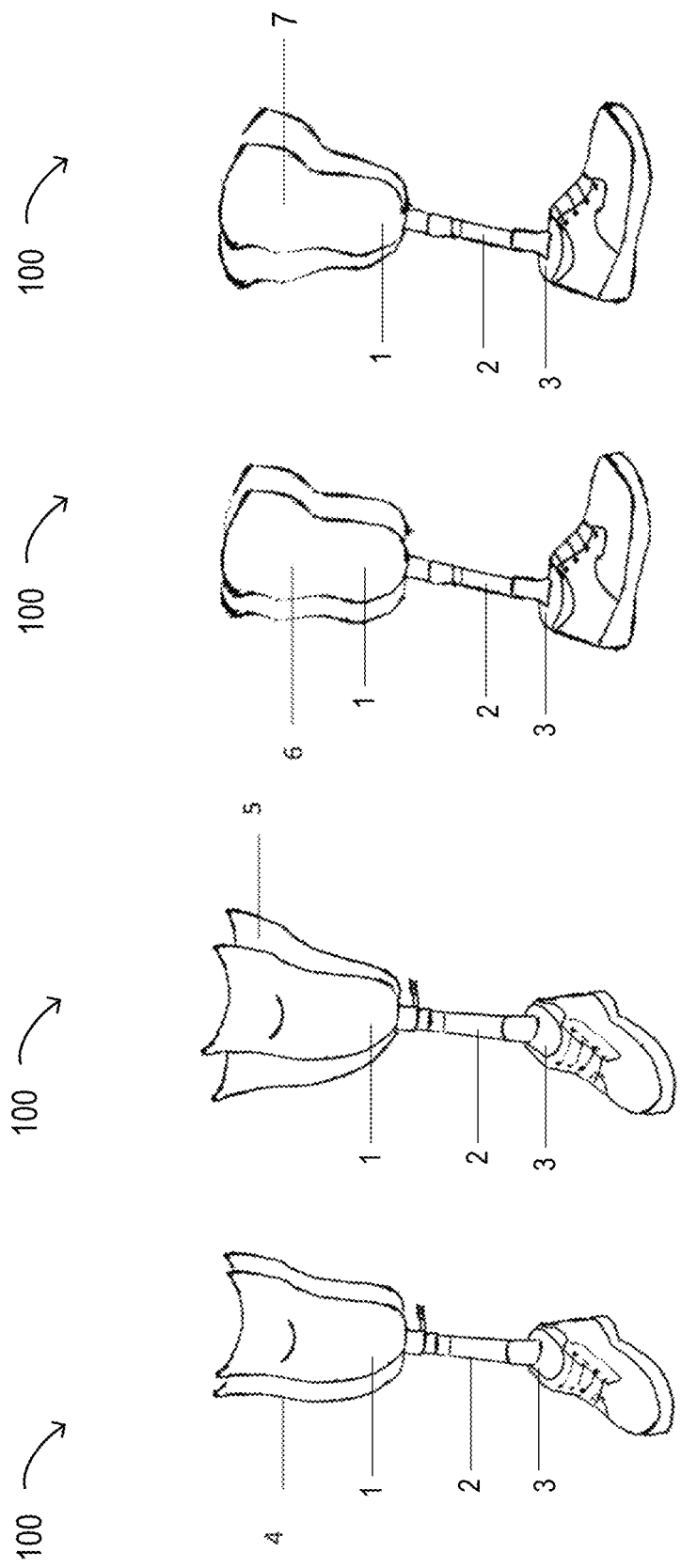

METHOD AND SYSTEM FOR ALIGNING A PROSTHETIC DEVICE

TECHNICAL FIELD

The present subject matter relates generally to a method of and system for facilitating prosthetic alignment, and more particularly to utilizing laser generating devices for aligning a prosthesis based on anatomical landmarks of the lower limbs.

BACKGROUND

Many accidents and diseases result in loss of a limb through amputations. Many of these amputations are for limbs of the lower extremities of the body. In an effort to improve the life of the person undergoing an amputation, significant research has been undertaken in developing artificial limbs that function like human limbs. These artificial limbs are often referred to as prosthetic devices, or prosthesis. Most prosthetic devices have a socket that attaches the prosthetic device to a residual limb of the amputee. Once it is attached, in order for the prosthetic device to function properly and comfortably the prosthetic device needs to be aligned properly relative to the user's body. Thus, alignment of a prosthesis is an important element of optimizing its function.

In common clinical practice, prosthetic alignment techniques primarily consist of three steps: bench alignment, static alignment and dynamic alignment. Bench alignment is generally done on a table without the user and may include attaching the socket to the rest of a prosthetic device at the proper location. Static alignment is normally performed in a standing position while the patient is placing weight on the prosthesis. The aim of static alignment is to make necessary corrections in height, inclination and translation to adjust the prosthesis to the specific biomechanical profile of the user before they take their first step with the device. Dynamic alignment is often done while the user is walking. For example, the prosthetist observes the amputee's walking quality and finetunes the prosthetic alignment to improve gait deviations. This step is repeated until both the amputee and the prosthetist determine that clinically acceptable alignment is achieved.

Most of these alignment steps are performed by visual estimation and take a long time to perform. As a result, prosthesis alignment has been an imprecise and inconsistent practice based primarily on subjective input from the amputee and the person performing the alignment. Because alignment relies primarily on the opinion of the technician performing the operation, it also generally requires a high level of expertise and experience and can thus become costly.

Therefore, a need exists for providing an improved method and system of facilitating alignment of a prosthetic device.

SUMMARY

A system for aligning a prosthetic device is provided. In one implementation, the system includes a support mechanism having an adjustable height attached to a laser generating unit, the laser generating unit configured for generating a horizontal laser beam, a base having a three-sided frame, wherein each of the three sides houses one or more sets of rail mechanisms, and an integrated scale having two identical scales attached to each other, wherein each set of the one more sets of rail mechanism includes at least two vertical beam generating laser units and one angular laser unit whose radius of radiation can be changed, and wherein each of the two vertical beam generating laser units is attached to a measuring device having an indicator for measuring a distance the vertical laser unit travels.

A method of aligning a prosthetic device is provided. In one implementation, the method includes determining if an adjustment of a height of the prosthetic device is needed based on a comparison of a location of an anterior superior iliac spine (ASIS) landmark on an uninjured leg side of a patient wearing the prosthetic device and a location of an ASIS landmark on an amputated side of the patient, and making the adjustment of the height, when needed, determining if an adjustment of an angle of a socket of the prosthetic device in the frontal plane is needed based on a comparison of an angle of a shin on the uninjured side and an angle of the socket on the amputated side, and making the adjustment of the angle of the socket, when needed, determining if an adjustment of an angle of a pylon of the prosthetic device in the frontal plane is needed based on a comparison of an angle of a shin on the uninjured side and an angle of the pylon on the amputated side, and making the adjustment of the angle of the pylon, when needed, determining if an adjustment of a position of a prosthetic foot of the prosthetic device in the frontal plane is needed and making the adjustment of the position of a prosthetic foot, when needed, determining if an adjustment of an angle of the socket in the sagittal plane is needed and making the adjustment of the angle of the socket in the sagittal plane, when needed, determining if an adjustment of an angle of the pylon in the sagittal plane is needed and making the adjustment of the angle of the pylon in the sagittal plane, when needed, determining if an adjustment of a horizontal position of the prosthetic foot in the sagittal plane is needed and making the adjustment of the horizontal position of the prosthetic foot in the sagittal plane, when needed, and determining if an adjustment of an angle of the prosthetic foot in a transverse plane is needed and making the adjustment of the angle of the prosthetic foot in a transverse plane, when needed.

BRIEF DESCRIPTION OF THE DRAWINGS

Features of the subject technology are set forth in the appended claims. However, for purpose of explanation, several implementations of the subject technology are set forth in the following figures.

FIGS. 2A-2G depict views of multiple changing positions for one or more parts of a prosthetic device.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings. As part of the description, some of this disclosure's drawings represent structures and devices in block diagram form in order to avoid obscuring the invention. In the interest of clarity, not all features of an actual implementation are described in this specification. Moreover, the language used in this disclosure has been principally selected for readability and instructional purposes, and may not have been selected to delineate or circumscribe the inventive subject matter, resort to the claims being necessary to determine such inventive subject matter. Reference in this disclosure to "one embodiment" or to "an embodiment" means that a particular feature, structure, or characteristic described in connection with the embodiment is included in at least one embodiment of the invention, and multiple references to "one embodiment" or "an embodiment" should not be understood as necessarily all referring to the same embodiment.

The solution proposed here provides an improved method of determining prosthetic alignment in three anatomical planes. By utilizing a system which includes multiple laser generating devices for producing horizontal and vertical laser beams and two integrated scales providing the amount of weight exerted by each limb of the user when standing, the method provides alignment based on the user's own anatomical landmarks. In one implementation, the system is used to determine proper coordinates for the prosthetic device based on various other coordinates of the injured or uninjured leg. Thus, in determining prosthetic alignment with the help of this system, horizontal distances and angles between the anatomical landmarks on the uninjured side of the body can be used to estimate corresponding values for the amputation side. In this process, the alignment of the prosthesis can be done accurately and in a short period of time.

Figures 1A, 1B:
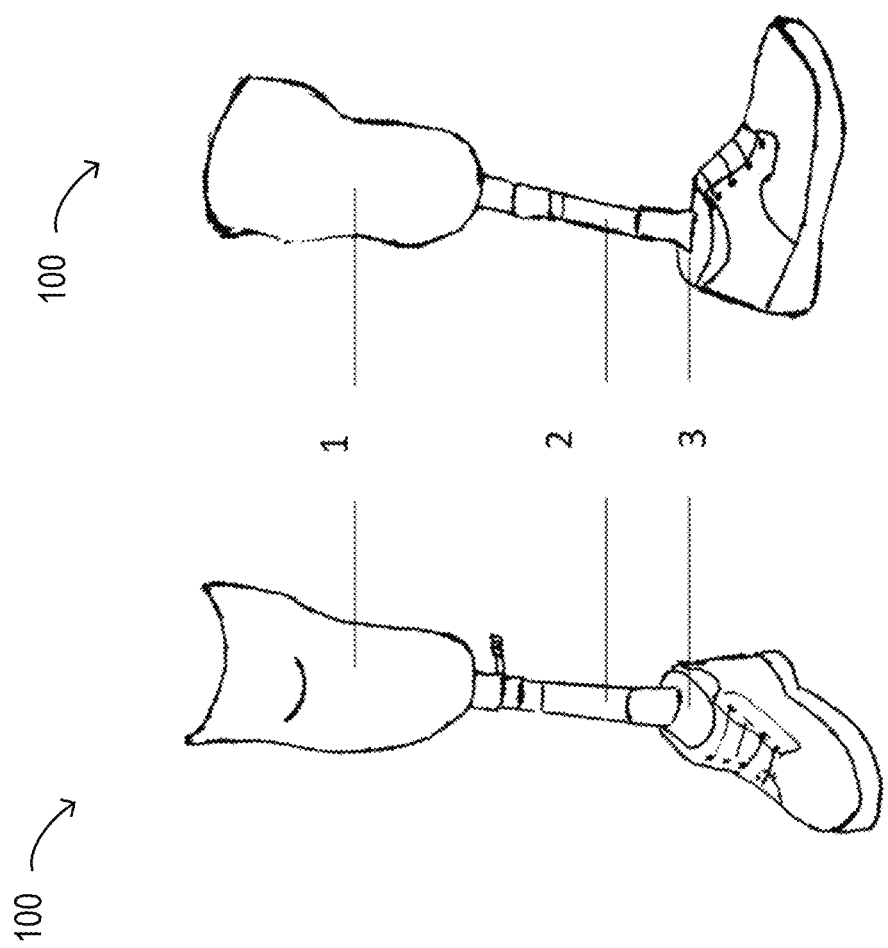
FIGS. 1A-1B depict a transtibial prosthetic device that can be aligned according to the improved method herein of determining prosthetic alignment.

FIGS. 1A-1B depict a transtibial prosthetic device 100 which can be aligned according to the improved method of determining prosthetic alignment disclosed herein. The prosthetic device 100 includes a socket 1, which is shaped like the shape of a residual limb and can be used to anchor the prosthetic device 100 to the residual limb of the user. The socket 1 is often custom made to fit the specific user and in particular to create a better fit between the residual limb and the prosthetic device.

In addition to the socket 1, the prosthetic device 100 includes a prosthetic foot 3 designed with properties that allow for stability and movement of the user, and to enable the user to walk. A pylon 2 of the prosthetic device 100 connects the socket 1 and the prosthetic foot 3 together. The pylon 2 may include multiple smaller adapters that are designed to help stabilize the prosthetic device and help in its proper alignment.

In one implementation, each of the three parts of the prosthetic device 100 is movable and/or adjustable. For example, the socket 1 may be rotatable in multiple directions and the pylon 2 may be adjustable in height. The prosthetic foot 3 may also be rotatable in the horizontal direction. As a result, alignment of the prosthetic device 100 may include changing the position of the socket 1 and the prosthetic foot 3 and/or adjusting the height of the pylon 2.

Figure 2G:
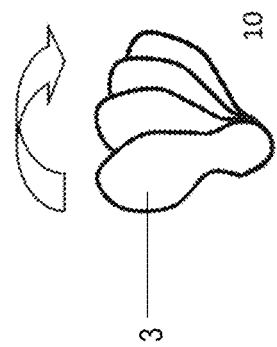

FIGS. 2A-2G depict multiple variable changing positions for one or more parts of the prosthetic device 100, in one implementation. For example, FIG. 2A depicts how socket 1 can have a displacement 4 in the frontal plane. As can be seen, socket 1 can be moved in the horizontal direction in the frontal plane to adjust its position. FIG. 2B depicts a tilt 5 of the socket 1 in the frontal plane. This shows that socket 1 can be tilted in the medial and lateral directions to adjust its position. FIG. 2C depicts a socket displacement 6 in the sagittal plane, while FIG. 2D depicts a socket tilt 7 in the sagittal plane. Thereby, socket 1 can be moved and tilted in both the frontal plane and sagittal plane to adjust its position.

Figure 2F:
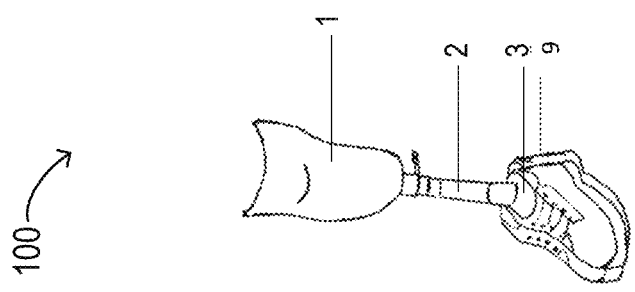
Figure 2E:
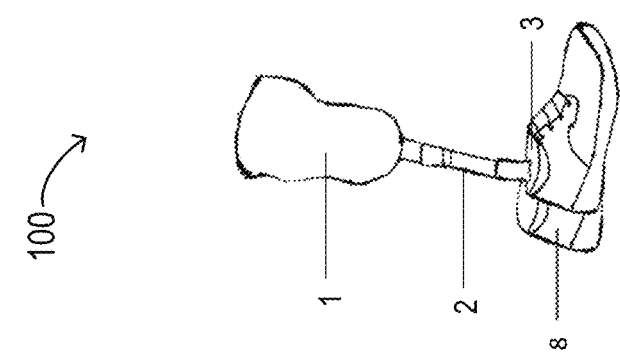

In addition to socket 1, prosthetic foot 3 can also be moved in both the frontal and sagittal planes. This is depicted in FIGS. 2E-2F. For example, FIG. 2E depicts how the prosthetic foot 3 can have a shift 8 in the sagittal plane. FIG. 2F, in turn, depicts how the prosthetic foot 3 can have a shift in position 9 in the frontal plane. In addition to moving in the frontal and sagittal plane, the prosthetic foot 3 can rotate in the transverse plane. This is depicted in FIG. 2G, which provides a view from the bottom of the prosthetic feet 3 and shows multiple shifts 10 of the prosthetic foot in the transverse plane.

Therefore, to properly align a prosthetic device, such as the prosthetic device 100 of FIGS. 1A-1B, in one implementation, proper position of the socket 1 and the prosthetic foot 3 in each of the frontal and sagittal planes is determined. Additionally, the proper tilt of the socket 1 in both the sagittal and frontal plane and the proper position of the prosthetic foot 3 in the transverse plane is identified. Moreover, the proper height of the prosthesis is determined and the height of pylon 2 adjusted accordingly.

In order to correctly measure the parameters for proper alignment in the improved method of determining prosthetic alignment disclosed herein, five main functions are provided: 1) the ability to measure the certain angles for both the uninjured leg and the amputated leg and to measure the angle of the socket 1 in both the sagittal and frontal planes, 2) the ability to compare a weight distribution between the uninjured leg and the amputated leg, 3) the ability to measure the horizontal distance between certain anatomical landmarks of lower limbs, 4) the ability to measure the position of the prosthetic feet 3 in the transverse plane; and 5) the ability to create a horizontal line to measure the alignment of the anterior superior iliac spine (ASIS) landmarks.

Figure 3:
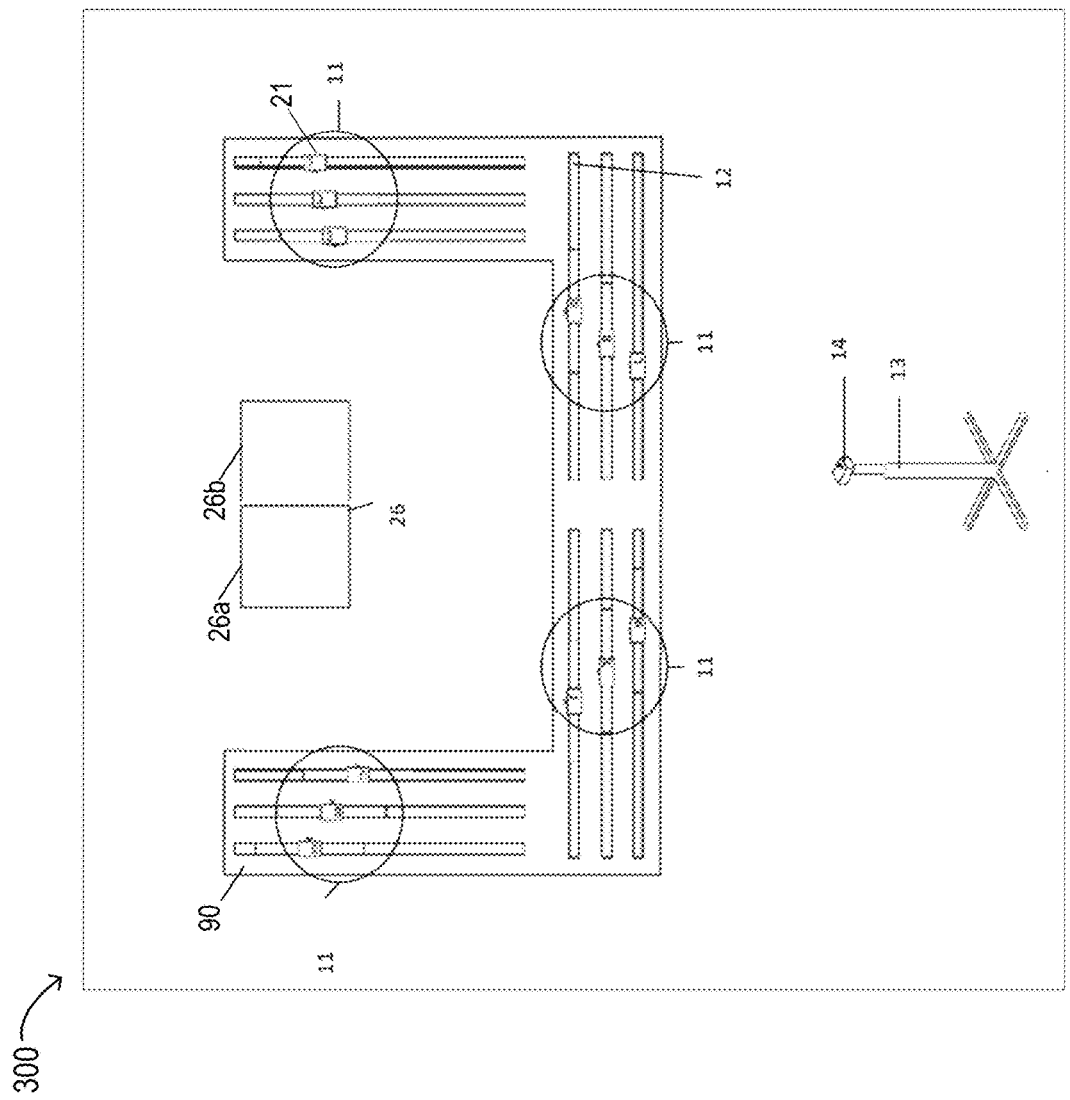
FIG. 3 is a view of a system for facilitating the improved method of determining prosthetic alignment.

These functions and more are provided, in one implementation by the system 300 of FIG. 3, which facilitates the improved method of determining prosthetic alignment disclosed herein. The system 300 includes a base 90, a scale unit 26 and a support mechanism such as the tripod 13 attached to a laser generating unit 14. The base 90 consists of a three-sided frame, each side of which houses multiple rail mechanisms 12. In one implementation, each of the left and right sides of the frame houses a set of three parallel rail mechanisms 12, while the middle section of the frame houses two sets of three parallel rail mechanisms 12. A movable laser generating unit 21 is positioned on each of the rail mechanisms 12, such that the rail mechanisms 12 facilitate linear movement of the movable laser units 21. The three movable laser units 21 in each set of three parallel rail mechanisms 12 form a unit 11.

The integrated scale 26 is positioned in between the two left and right sides of the three-sided frame, and in one implementation, is located in the middle of the two sides such that it faces the middle section of the three-sided frame. The integrated scale 26 includes a left scale 26a and a right scale 26b that are connected to form an integrated scale 26. The tripod 13 is positioned such that it faces both integrated scale 26 and the middle section of the three-sided frame. In one implementation, the tripod 13 has an adjustable height. The laser generating unit 14 produces a horizontal laser beam. The laser unit 14 is similar in terms of electronic structure to each of the movable laser units 21.

Figure 4:
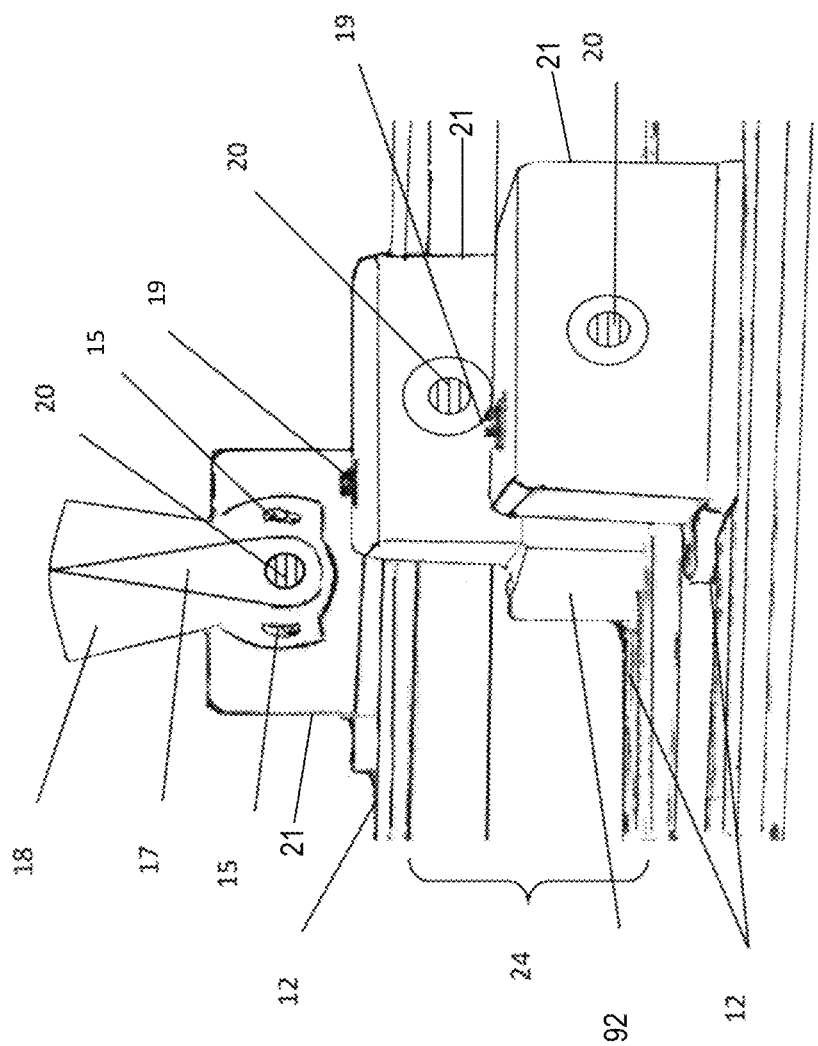
FIG. 4 is a front perspective view of a set of laser beam generating units.

FIG. 4 depicts a front view of a unit 11. The unit 11 includes three movable laser generating units 21. In one implementation, the movable laser units 21 are identical in terms of the laser module and structure. Each laser module unit 21 includes a laser beam diode 20 for generating a laser beam and a power switch 19 for turning the laser beam diode 20 on and off. Because the laser units 21 are movable, the ones in front could potentially block the laser beam generated by one or more of the movable laser units 21 in the back. In order to prevent this, the height of each movable laser unit 21 in the unit 11 is different from the others. In one implementation, the movable laser unit 21 closest to the integrated scale 26 has the lowest height and is positioned directly on the rail mechanism 12. The movable laser unit 21 behind the closest movable laser unit 21 is located at a higher elevation than the rails with the help of a block 92. These two movable laser units 21 generate vertical laser beams. The highest movable laser unit 21 is at the very back and includes a laser beam diode 20 whose radius of radiation can be changed. This laser unit 21 may be referred to as an angular laser unit. In one implementation, to ensure that the movable laser unit 21 at the back has the highest height, the movable laser unit 21 is positioned on a raised platform 24. The raised platform 24 is installed such that its laser beam diode 20 of the highest movable laser unit 21 is located above the top edge of the other two movable laser units 21.

In one implementation, the highest movable laser unit 21 is attached to a member 18 having a pointer 17 and two knobs 15. The top surface of the member 18 includes markings 74 (shown in FIG. 6) for identifying corresponding angles for various positions of the pointer 17. In one implementation, the markings 74 show a range of 40 degrees with the center position being at 0 degrees. The knobs 15 can move the member 18 with respect to the movable laser unit 21. For example, the position of the member 18 can be adjusted by utilizing the knobs 15 such that the zero degree position shown in the markings 74 is perpendicular to the ground. The pointer 17 is connected to the beam outlet of the laser beam diode 20. As a result, turning the pointer 17 can change the angle of the produced laser beam. For example, depending on which degree of the pointer 17 is placed next to the degree markings 74, the angle of the produced laser beam can be changed by 90 degrees. In one implementation, the angle ranges from 70 to 120 degrees.

Figure 5:
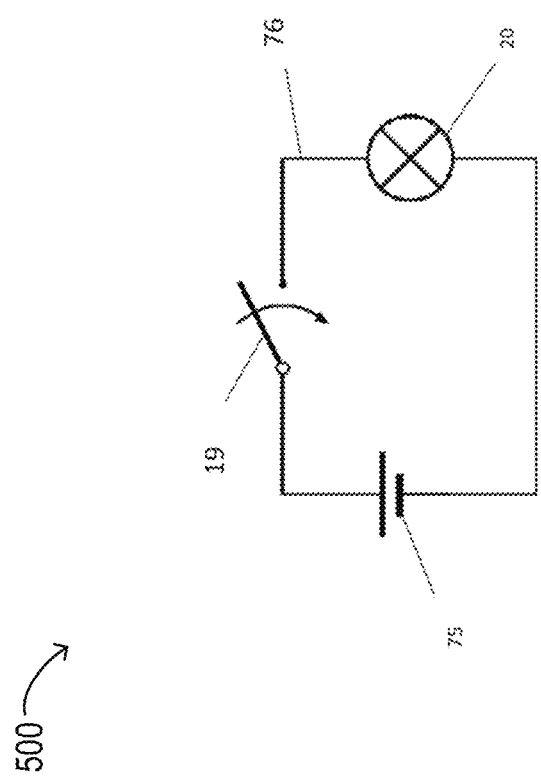
FIG. 5 is a schematic drawing of a circuit for utilizing a laser beam diode.

FIG. 5 depicts a schematic of a circuit 500 for utilizing the laser beam diode 20. The circuit 500 includes a power supply 75 for providing power on line 76 to the laser beam diode 20 and the switch 19 for turning the laser beam diode 20 on and off. The power supply 75 can be any suitable source of power. For example, the power supply can be a battery. In one implementation, the battery is a three-volt battery with a capacity of 90 amps. The laser beam diode 20 can be a linear laser beam diode. The circuit 500 may represent both a laser beam diode 20 of the movable laser units 21 and the laser beam diode of the laser unit 14. The difference between the vertical laser units 21 and the horizontal laser unit 14 is in the direction of the generated laser beam.

Figure 6:
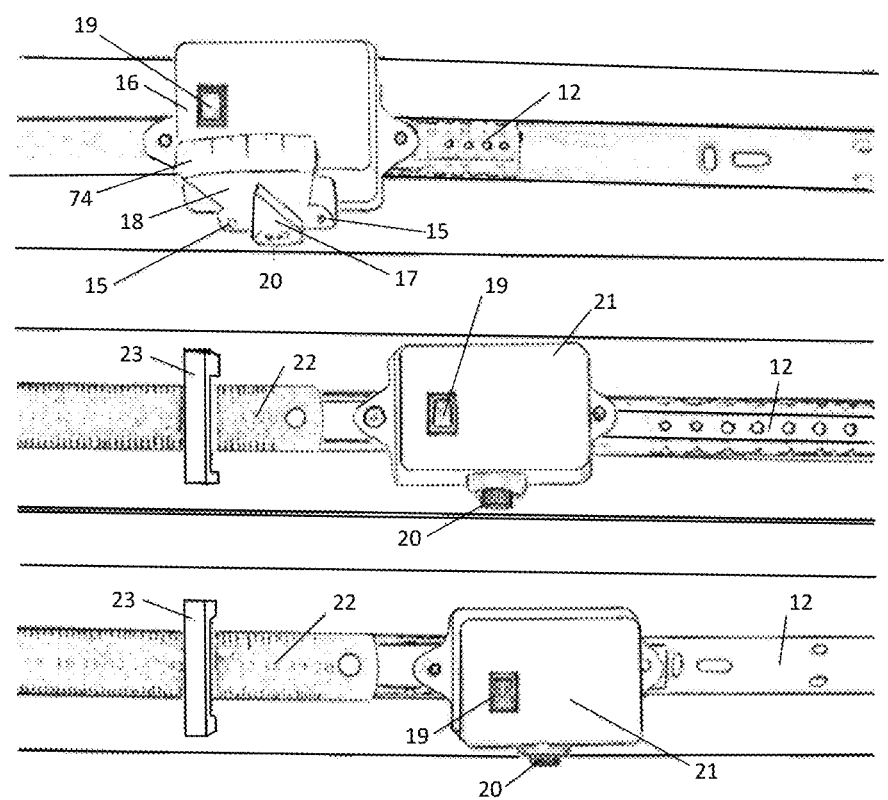
FIG. 6 is a top view of set of laser beam generating units.

FIG. 6 depicts a top view of the unit 11 as positioned on the rail mechanisms 12. The top view illustrates a top surface of each of the movable laser units 21 along with the markings 74 of the element 18, and three rail mechanisms 12. In cases where vertical beam generating laser units 21 are installed on the rail mechanism 12 (i.e., the two front movable laser units 21) a measurement device such as ruler 22 is positioned on the rail mechanism 12 adjacent to the movable laser unit 21. In one implementation, the ruler is a smaller ruler of a length of approximately 20 cm. The ruler is movable on the rail mechanism 12 such that when the movable laser unit 21 moves, the ruler moves with it, thus changing the position of the ruler with respect to a stationary indicator 23. The stationary indicator 23 is attached to the sides of the railing mechanism 12 and is used to identify a change in the position of the ruler and thus make measurements. In this way, the horizontal displacement of the movable laser units 21 and thereby the laser beams can be calculated according to the amount of change in the position of the ruler 22 relative to the indicator 23. When the position of the two front movable laser units 21 is the same on the rail mechanism 12, the rulers 22 will also show the same numeric indicator 23. When the movable laser units 21 move to their original position, the difference between the rulers 22 and the indicator 23 is the same as the distance between the two vertical beams produced by the movable laser units 21.

Figure 7A:
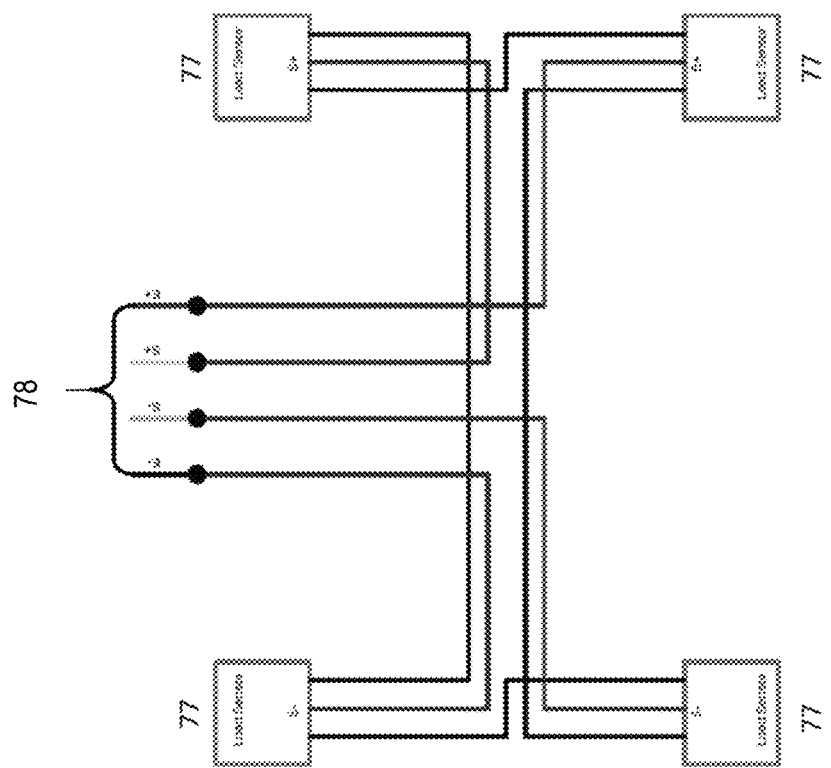
FIGS. 7A-7B are schematic drawings showing portions of the internal circuitry of one of the integrated scales and a digital-to-analogue convertor module that are a part of the system for facilitating the improved method of determining prosthetic alignment.
Figure 7B:
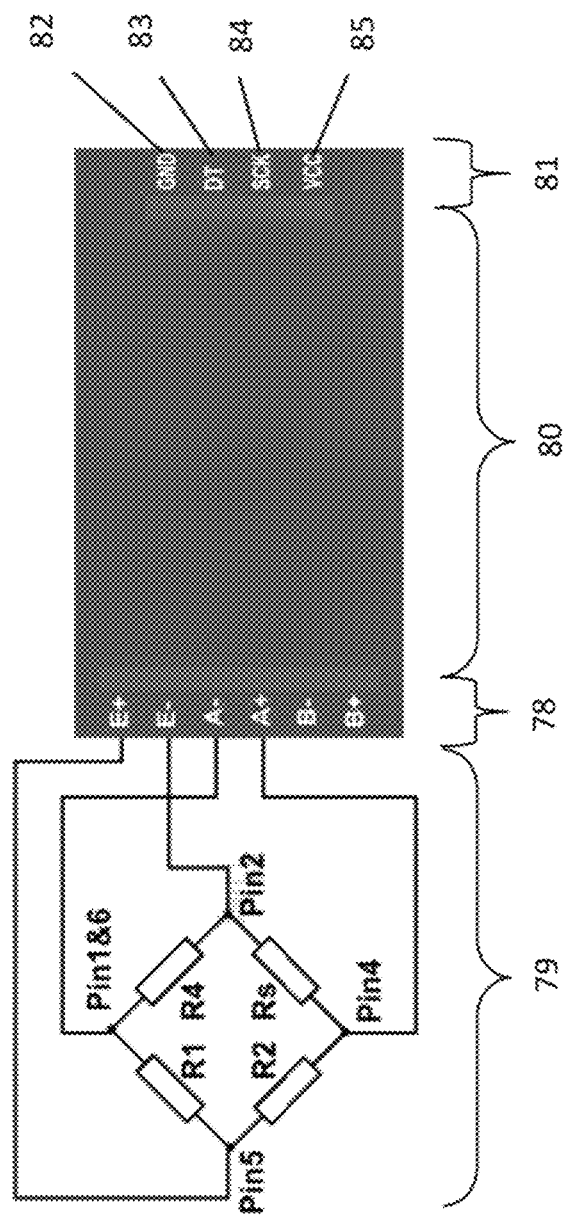

FIG. 7A is a simplified schematic showing a portion of the internal circuitry of one of the scales (either 26a or 26b) that form the integrated scale 26. Each scale 26a (or 26b) includes four load sensors 77, each of which have three outputs. Two of the outputs from each load sensor 77 are connected to two other load sensors 77, while one output is received as one of multiple inputs of an input module 78. In one implementation, each load sensor 77 is a strain gauge load cell. Deformation of the strain gauge changes the electrical resistance of the load sensor 77, by an amount that is proportional to the strain. Each load sensor 77 may act as one of four resisters of a Wheatstone bridge 79 (as shown in FIG. 7B). One output of each load sensor 77 may connect through the input module 78 to a digital-to-analogue convertor module 80 (shown in FIG. 7B).

FIG. 7B is a simplified schematic of another portion of the internal circuitry of one of the scales 26a or 26b. The inputs 78 carrying output signals from the load sensors 77 enter the digital-to-analog convertor module 80, which, in one implementation, is a 24-bit digital-to-analog converter. The input module 78 may have a 6-pin header for connecting to the load sensors 77 and a 4-pin header for connecting to a microcontroller circuit (not shown). In one implementation, the microcontroller circuit is an Arduino module, which is programmed to control the load sensors 77 and to send information to a computer. The Wheatstone bridge 79 depicts a schematic view of the body scale, as each load sensor 77 of the scale acts as one of four resisters of the Wheatstone bridge 79. The digital to analogue convertor 80 sends data to the data controller module from the output 81. In one implementation, the analog-to-digital converter has a precision of 24 bits and a maximum sample rate of 80 samples per second. The analog-to-digital converter includes a data output line 83, a clock line 84, a ground line 82 and a voltage supply line 85. The analog-to-digital converter is also connected to the microcontroller (not shown) which controls the operation of the scale 26a or 26b.

Figure 8:
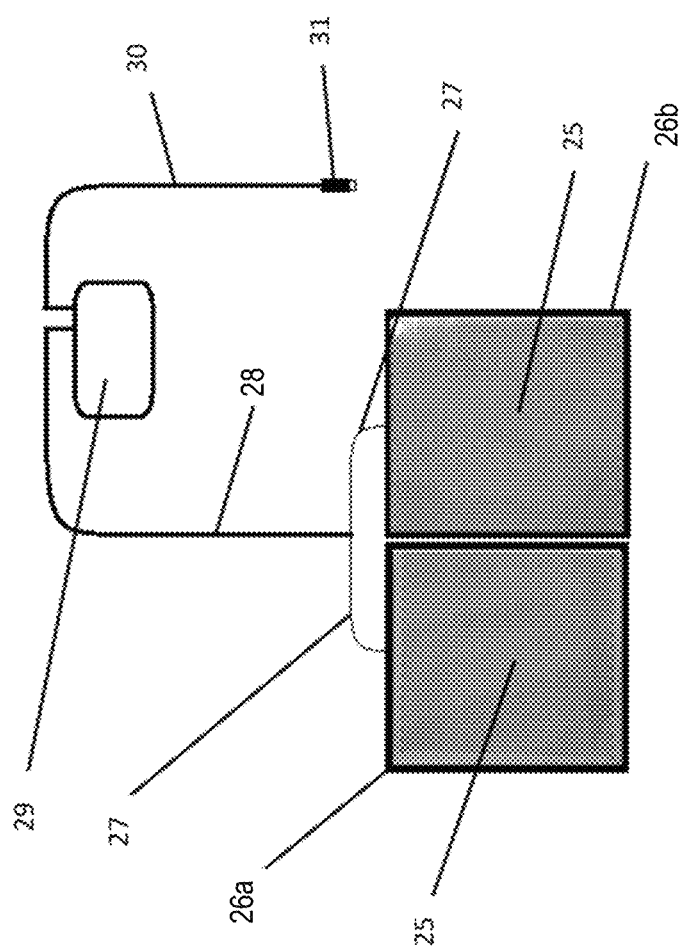
FIG. 8 is a top view of the integrated scale.

FIG. 8 depicts a top view of the integrated scale 26. As shown, the integrated scale 26 includes two scales 26a and 26b for simultaneously measuring the weight of each leg. Each of the two scales 26a and 26b is covered by a coordinate plate 25. Each scale 26a and 26b includes an output 27. An intermediary connector 28 functions as the interface between the data convertor module and the output 27 of each scale 26a and 26b. The connector 28 may be a cable having two identical input ports for connecting to the outputs 27. Each output signal 27 contains the output information for each scale 26a and 26b. After processing the data in the analogue-to-digital convertor and then data controller modules, an output cable 30 carries the signal to the connector 31, which is configured to connect to a computer. The connector 31 may be a USB port or any other port that can be used to directly connect the scale 26 to a computing device. A data protection module 29 is used to protect the two modules. Therefore, the integrated scale 26 provides two identical digital scales 26a and 26b that can simultaneously measure the amount of weight excreted by the user's leg and the prosthetic device with high precision. In one implementation, the integrated scale 26 has a precision of 50 grams.

Figure 9:
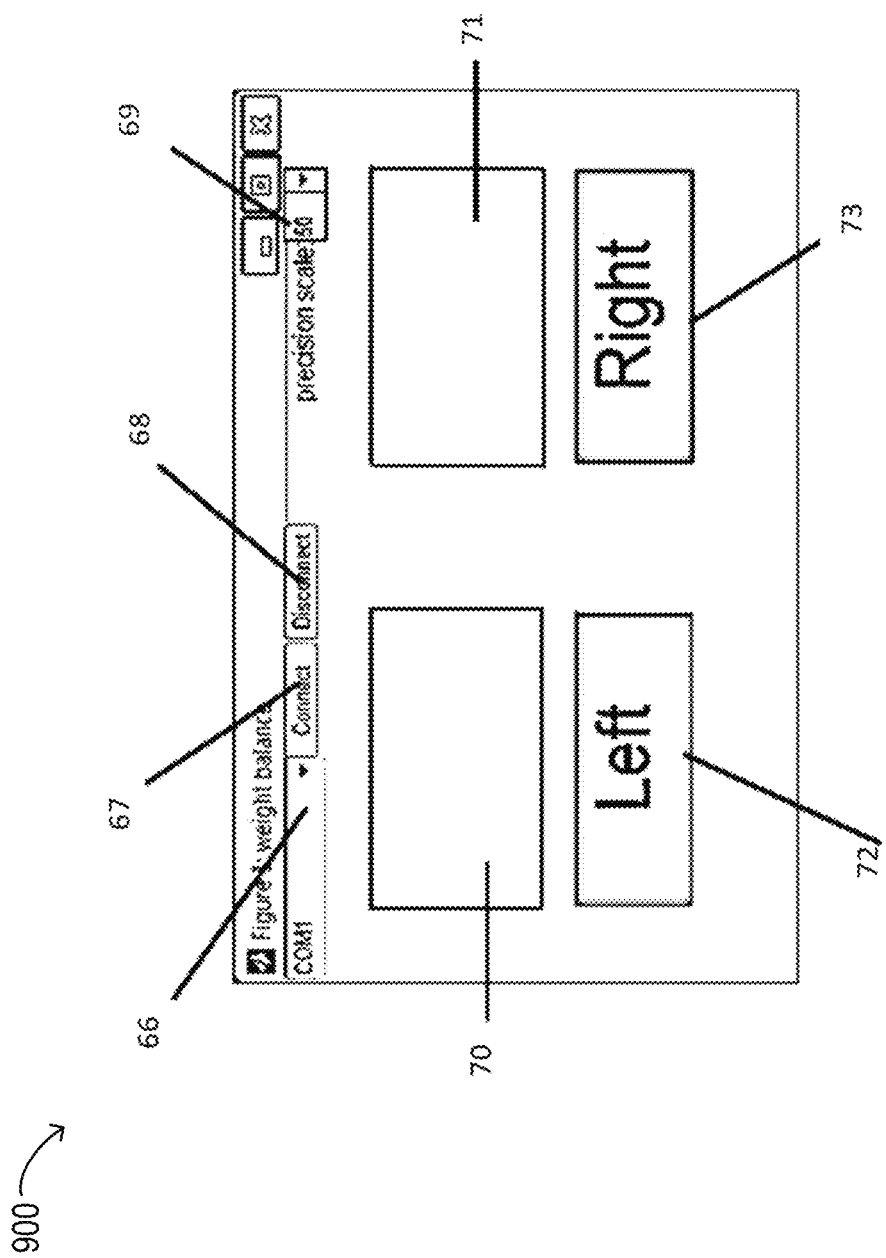
FIG. 9 is an illustration of a graphical user interface used to facilitate interactions between a user of a computer and the integrated scale.

FIG. 9 depicts a graphical user interface (GUI) 900 used, in one implementation, to facilitate interactions between a user of a computer and the integrated scale 26. The graphical user interface 900 may be generated through a software program developed for performing the improved method of determining prosthetic alignment disclosed herein. Alternatively, the software program may be related to the integrated scale 26 and separate from any other programs relating to the improved method of determining prosthetic alignment.

In one implementation, the GUI 900 appears on a display of a computing device upon starting the software program. Alternatively, the GUI 900 may appear on the screen upon connecting the connector 31 to the computing device. The GUI 900 includes a dropdown box 66 for presenting a list of devices to which the computing device may be connected. A user of the computing device can select the appropriate choice that corresponds to the integrated scale 26, using the dropdown box 66. Buttons 67 and 68 can be used to connect and disconnect, respectively, the computing device to the integrated scale 26. Upon connecting the computing device to the integrated scale 26, the weight registered by the scale 26a may be displayed in the box 70, while the weight registered by the scale 26b may be displayed in the box 71. The labels 72 and 73 identify which of the scales each of the boxes 70 and 71 relate to. The GUI 900 also includes a dropdown box 69 for selecting a precision scale for the integrated scale 26. In this manner, the amount of precision of the integrated scale 26 can be changed.

Figure 10:
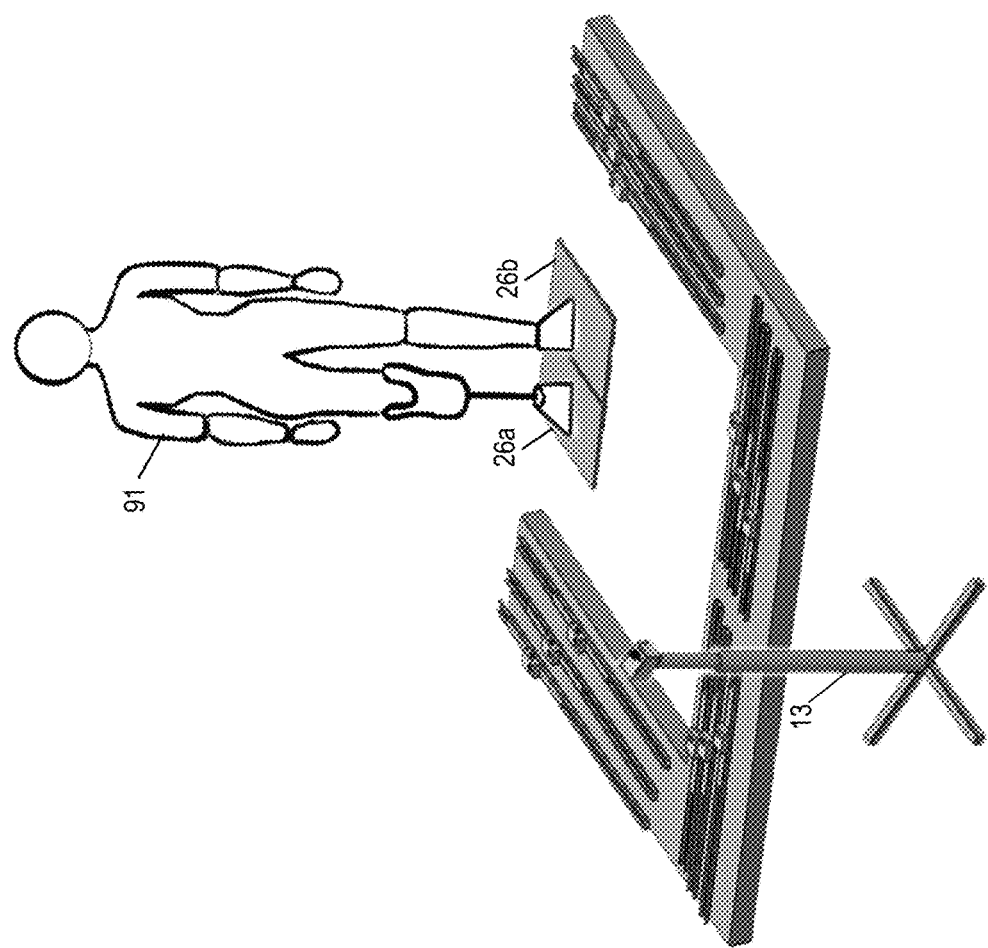
FIG. 10 is a schematic view depicting a position of a patient with a prosthetic device during the improved method of determining prosthetic alignment.

The process of aligning a prosthetic device often requires the user to wear the device and stand on it, without performing a dynamic alignment which often requires walking with the prosthetic device. The improved method of performing prosthetic alignment disclosed herein, however, involves wearing the prosthetic device and standing on a scale while an attempt is made to apply a uniform distribution of weight on the prosthetic device and the uninjured leg. FIG. 10 illustrates how this may be done, in one implementation. As shown, a user 91 stands on the integrated scale 26 while facing the tripod 13, by placing the prosthetic device on scale 26a and placing their uninjured leg on the scale 26b.

Figure 11:
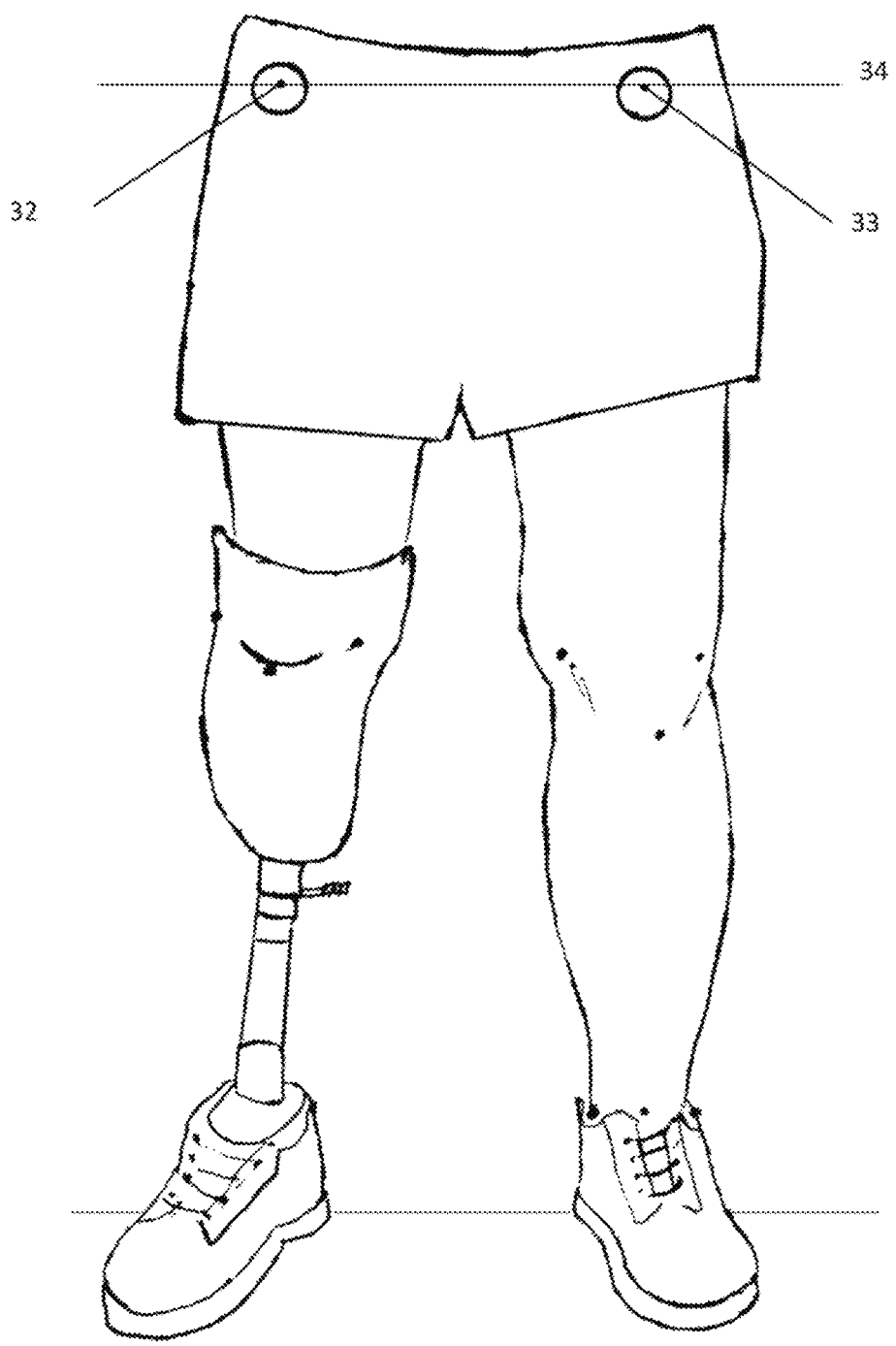
FIG. 11 depicts one or more steps in the process of determining a proper height for the prosthetic device.

In one implementation, the first step in performing prosthetic alignment is determining the correct height for the prosthetic device. This is done by examining the alignment of the ASIS landmarks, as depicted in FIG. 11. The process involves first determining the location of a right ASIS anatomical landmark 32 and a left ASIS anatomical landmark 33. To do this, the patient may be required to lie on their back while the technician locates the anatomical landmarks. The ASIS anatomical landmarks can be found along the proximal of inguinal ligament and are characterized by their roundness and stiffness. Other known methods of locating the ASIS anatomical landmarks may also be used. Once the right ASIS anatomical landmark 32 and a left anatomical landmark 33 are located, they may be marked on the patient using a marker, stickers or other methods, before the patient gets up to stand on the prosthetic device. Once standing, the patient faces the tripod 13, while staying within a predetermined distance from the laser unit 14. In one implementation, the patient may stand adjacent to the scale 26. The laser unit 14 is then turned on to project a horizontal beam 34 on the patient. The height of the tripod 13 may be adjusted, at this point, to ensure the horizontal beam 34 crosses the left ASIS anatomical landmark 33. If the horizontal beam 34 crosses the right ASIS anatomical landmark 32, while crossing the left ASIS anatomical landmark 33, then the prosthetic device has an appropriate height. Otherwise, the height of the prosthetic device is adjusted until horizontal beam 34 crosses both the left and the right ASIS anatomical landmarks 32 and 33. This is because the clinical criterion for assessing the length of the right and left legs is the horizontal alignment of the ASIS anatomical landmarks in the frontal plane. As a result, the length of the prosthesis is considered appropriate, in one implementation, if the horizontal deviation of the left and right ASIS anatomical landmarks is 1 degree or less.

Figure 12:
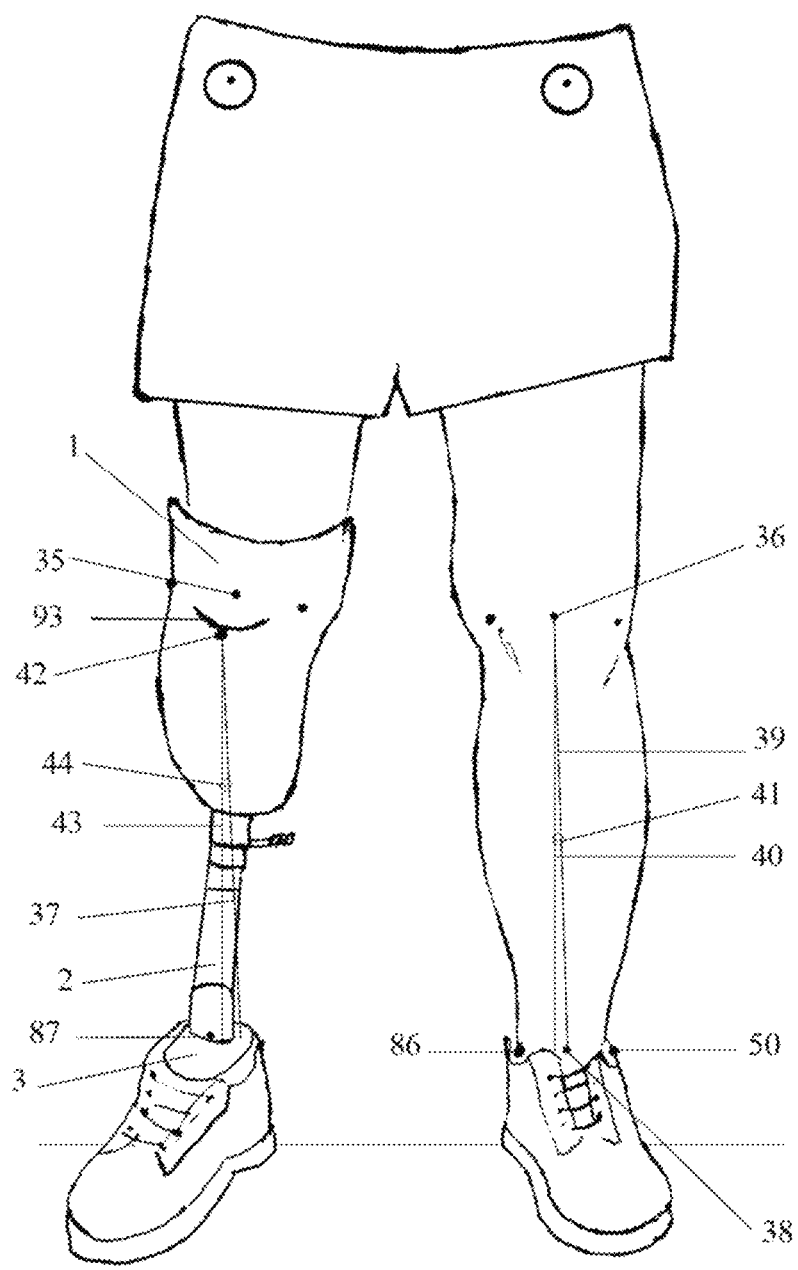
FIG. 12 depicts one or more steps in the process of determining a correct angle for a socket of the prosthetic device in the frontal plane.

After the correct height of the prosthetic device has been determined, one of the next steps in the process of performing prosthetic alignment is determining a correct angle for the socket of the prosthetic device in the frontal plane. This is performed by measuring and comparing angles on both the uninjured side and the amputated side, as depicted in FIG. 12. For this purpose, the location of the knee joint and its midpoint 36 in the frontal plane, as well as the midpoint 38 of the ankle joint in the frontal plane are first identified.

To find the location of the knee joint, first the anterior border of the Tibia plateau is identified. One way to do that is by touching the tip of your fingers at the side of the inner edge of the patella and continuing to move your fingers down along the same line to find the Tibia plateau. Another method for finding the Tibia is to have the patient sit at the edge of a chair or table and bend their knee. In this situation, with a slight stretching down of the shin, the knee joint space can be located. In one implementation, the technician locates and marks the proximal Tibia plateau twice with a marker, such as, an ultraviolet pen. If the marks are the approximately the same both times, then a fix marks may be made on the medial and lateral borders of Tibia. The midpoint 36 of the knee joint can then be determined between the two marks, while the patient is flexing their shin down by using a long jaw caliper. This method is known in the art and described in detail at "Reichert, B., & Stelzenmueller, W. (2011b). Knee Joint *Palpation Techniques: Surface Anatomy for Physical Therapists* (pp. 131): Thieme," the entirety of which is incorporated herein by reference. After the midpoint 36 is identified, the midpoint 38 of the ankle is identified by first locating the medial malleolus 86 and the lateral malleolus 50 and then using a long jaw caliper to identify the midpoint between them.

Once the midpoints 36 and 38 are identified and marked on the patient, an angular laser unit can be used to generate a laser beam 39 that connects the midpoint 36 to the midpoint 38. A vertical beam generating laser unit is then used to generate a vertical line 40 originating from the midpoint 36 that helps measure the shin angle 41 of the uninjured leg in the frontal plane. The angle 41 between the beams 40 and 39 is then determined based on the location of the pointer 17 with respect to degree markings 74.

The inventors have determined that the shin angle 41 can be used to determine the proper angle for the socket 1 of the prosthetic device. As a result, once the angle 41 is measured, the technician proceeds to the determine the angle 44 of the socket in the frontal plane. This is done, in one implementation, by first identifying the midpoint 42 of the patellar shelf 93 on the socket 1 using a long jaw caliper.

To measure the angle of the socket on the frontal plane, a vertical line 44 starting from the midpoint 42 is first generated by a vertical laser unit. Then, the angular laser unit whose radius of radiation can be changed is used to generate a laser beam 37 that starts at the midpoint 42 to the end of the socket 1 in the frontal plane. To identify the end of the socket in the frontal plane, the distal socket in the frontal plane, which is positioned vertically below the patella 93, is located using a long jaw caliper. The angle 44 between the two lines 43 and 37 is then measured to determine the angle of the socket 1 in the frontal plane. If the difference between the angle 44 and the angle 41 is larger than a predetermined threshold, then the patient removes the prosthesis and the angle of the socket is adjusted according to the difference between the angles. That is because, it has been determined that for proper alignment, the angle of the socket should be as close to the shin angle of the uninjured leg as possible. Once the angle of the socket is changed, the patient can put on the prosthesis and have the angle measured again to confirm correspondence between the new angle of the socket and the angle of the uninjured leg.

Figure 13:
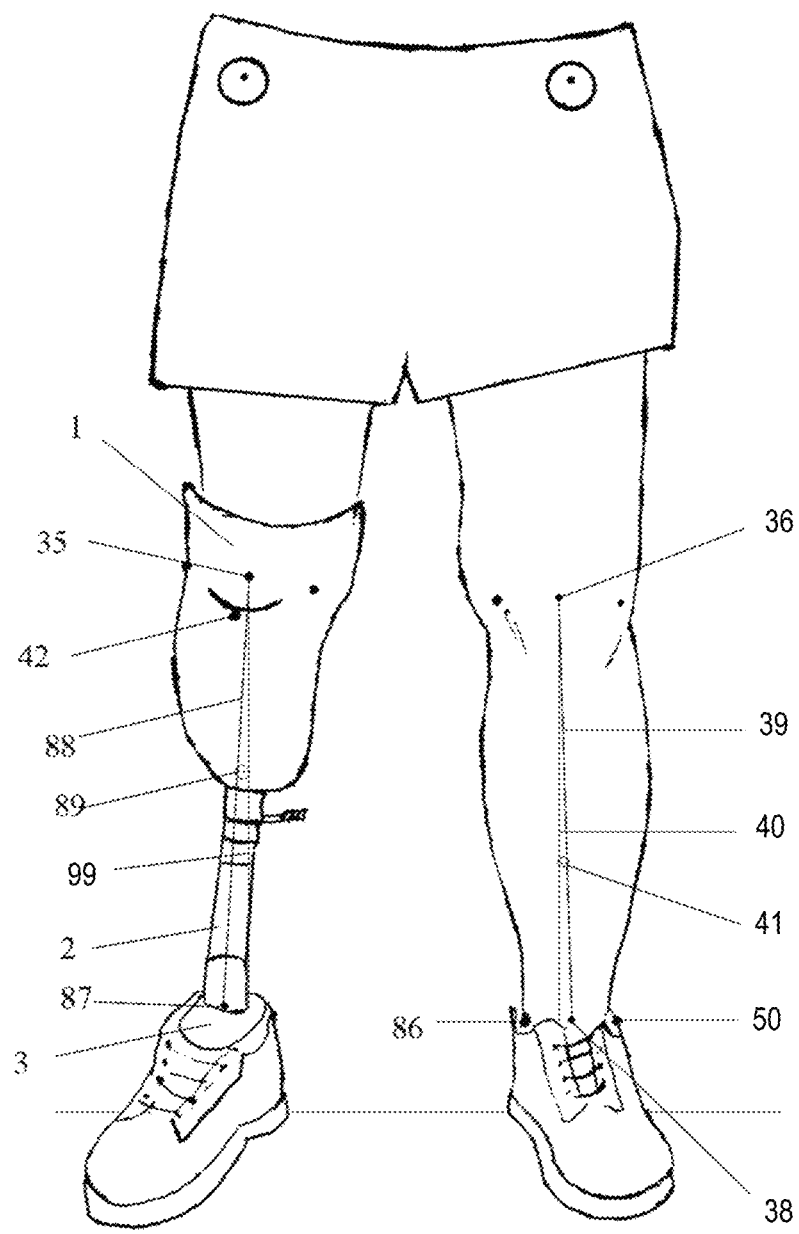
FIG. 13 depicts one or more steps in the process of determining a correct angle for a pylon of the prosthetic device in the frontal plane.

The inventors have determined that the shin angle 41 can also be used to determine the proper angle for the pylon 2 of the prosthetic device. As a result, once the angle 41 is measured, the technician proceeds to the determine the angle 89 of the pylon in the frontal plane, as illustrated in FIG. 13. This is done, in one implementation, by first identifying the midpoint 35 of the knee joint on the amputation side. This can be done, in a similar manner as described above for the uninjured side. Then, the knee joint can be extended and two horizontal lines can be marked from the knee joint up to a point about 20 cm above the knee joint at the medial and lateral sides. In one implementation, this is with the help of an ultraviolet pen for efficiency. The patient can then put the prosthesis on, stand on so it is firmly put in place, sit on a bed and then extend the prosthesis up. The ultraviolet line from the thigh is then lowered onto the socket 1, to identify the location of the knee joint on the socket. Finally, the midpoint 35 of the socket can be determined at the knee joint level using a long jaw caliper.

To measure the angle of the pylon 2 on the frontal plane, a vertical line 99 starting from the midpoint 35 is first generated by a vertical laser unit. Then, the angular laser unit whose radius of radiation can be changed is used to generate a laser beam 88 that starts at the midpoint 35 to the end of the pylon 87 in the frontal plane. To identify the end of the pylon in the frontal plane (the point at which the pylon attaches to the prosthetic foot), which is the middle point below the patellar shelf 93, a long jaw caliper may be used. The angle 89 between the two lines 88 and 99 is then measured to determine the angle of the pylon 2 in the frontal plane. If the difference between the angle 89 and the angle 41 is larger than a predetermined threshold, then the patient removes the prosthesis and the angle of the pylon is adjusted according to the difference between the angles. That is because, it has been determined that for proper alignment, the angle of the pylon should be as close to the shin angle of the uninjured leg as possible. Once the angle of the pylon is changed, the patient can put on the prosthesis and have the angle measured again to confirm correspondence between the new angle of the pylon and the shin angle of the uninjured leg.

Figure 14:
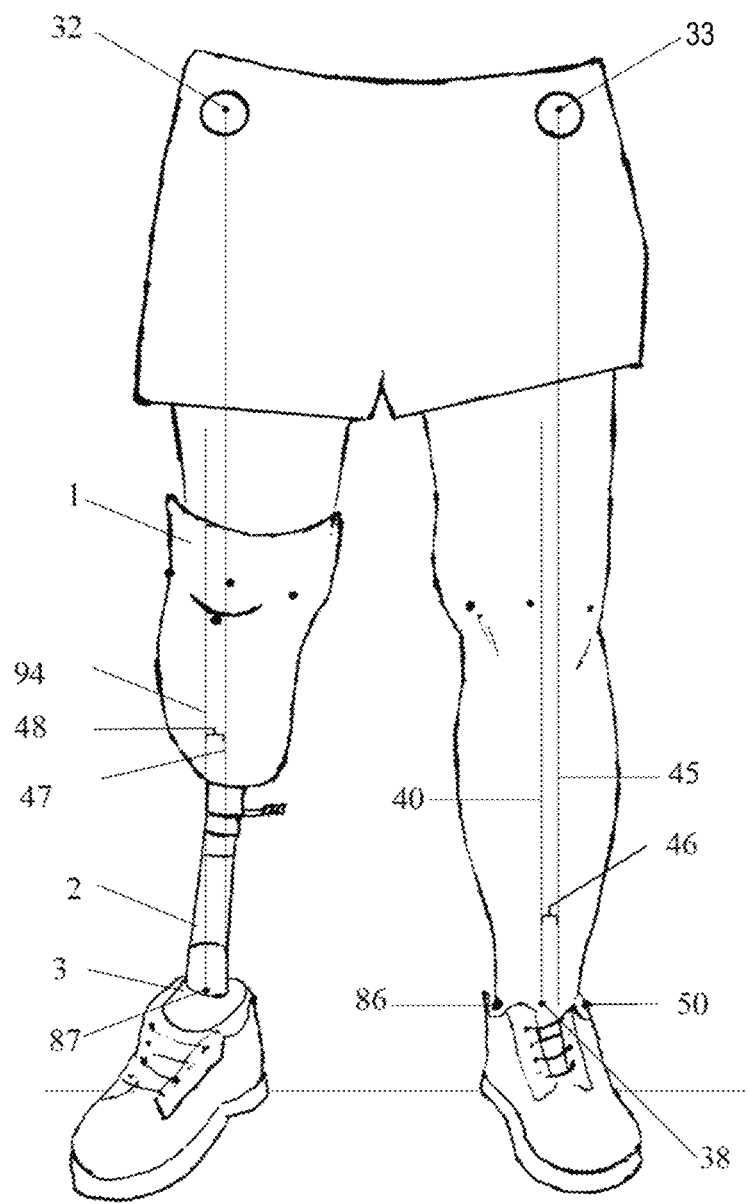
FIG. 14 depicts one or more steps in the process of determining proper alignment of a prosthetic foot in the frontal plane.

FIG. 14 depicts the process for determining proper alignment of the prosthetic foot in the frontal plane. This process involves measuring the distance 46 between the vertical lines 45 and 40, measuring the distance 48 between the vertical lines 94 and 47, and ensuring that two distances are approximately equal. To do this, first a vertical beam generating laser unit is used to generate the laser beam 45 from the ASIS anatomical landmark point 33. Then, using the same vertical laser unit another vertical beam 40 is generated that passes through the midpoint 38. This causes, the ruler 22 (of FIG. 6) to move with respect to the indicator 23 (of FIG. 6), thus providing the distance 46 that corresponds to the distance between the vertical beams 40 and 45. Next, the distance 48 is determined for the amputation side in a similar manner, by first generating a vertical beam 47 that passes through the ASIS anatomical landmark 32, then using the same laser unit to generate a vertical beam 94 that passes through the midpoint 87, and determining the distance 48 using the indicator 23 of the ruler 22. If these two distances are not substantially equal, then the horizontal position of the prosthetic device on the frontal plane is modified with the aim of equalizing the values for the distances 46 and 48, until the desire result is achieved.

Figure 15:
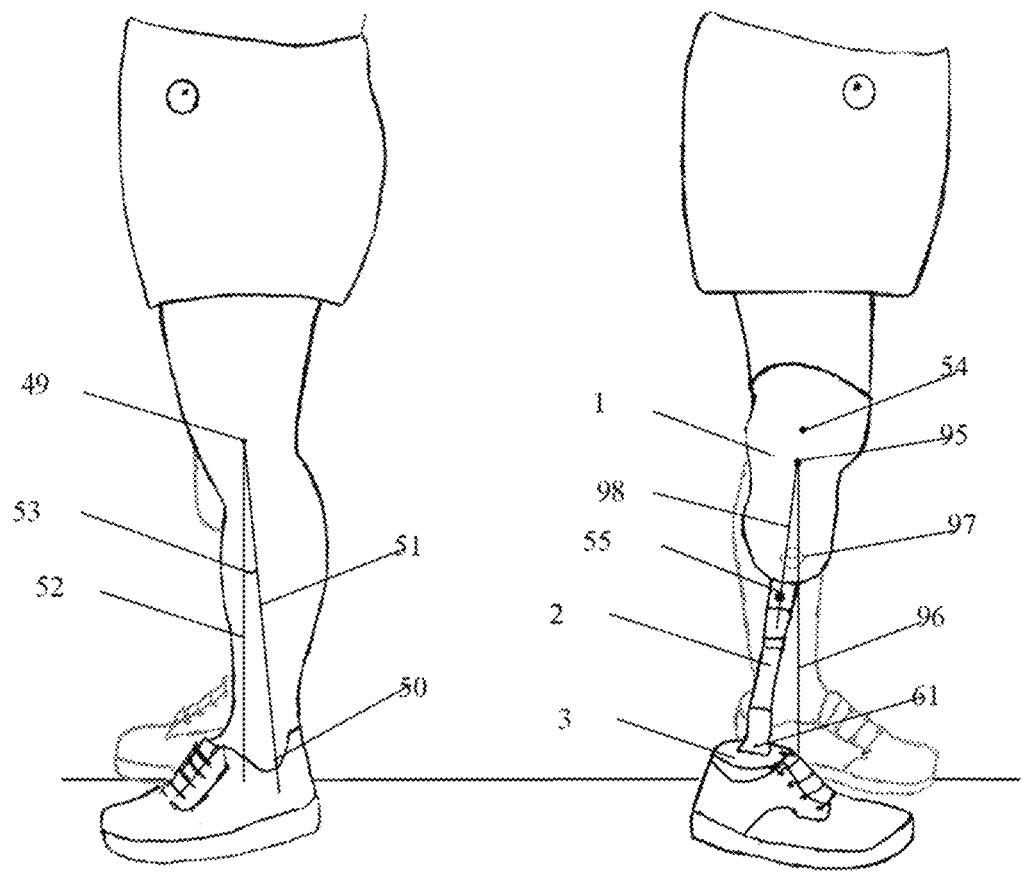
FIG. 15 depicts one or more steps in the process of determining proper alignment of the angle of the socket of the prosthetic device in the sagittal plane.

The next step in the process of prosthetic alignment involves evaluating the angle of the socket 1 in the sagittal plane and correcting it, if needed, as depicted in FIG. 15. This requires measuring the angle on the uninjured side. For this purpose, the midpoint 49 of the knee joint in the sagittal plane is identified using a long jaw caliper, while the patient is standing. Once the midpoint 49 is identified, a straight vertical beam 52 in the sagittal plane which starts at the midpoint 49 is generated. Then, an angular laser unit whose radius of radiation can be changed is used to generate a laser beam 51 which starts at the midpoint 49 and is extended to pass through the lateral malleolus 50. The angle 53 between the two beams 52 and 51 is then measured.

The midpoint 95 of the socket 1 at the patellar shelf level 93 in the sagittal plane is identified using a long jaw caliper, while the patient is standing. Once the midpoint 95 at the patellar shelf level is identified, a straight vertical beam 96 in the sagittal plane, which starts at the midpoint 95 is generated. An angular laser unit whose radius of radiation can be changed is used, next, to generate a laser beam 98 which starts at the midpoint 95 and is extended to pass through the midpoint 55 in the sagittal plane that is located between the socket 1 and the pylon 2. This helps the technician measure the angle 97. According to experiments performed by the inventors of the current application, best alignment results are achieved when the angle 97 is a multiple of the angle 53. For example, the angle 58 may be 57% larger than the angle 53. If the measured angles do not comply with these requirements, the prosthesis is removed and the angle of the socket is adjusted as needed to obtain the desired results.

Figure 16:
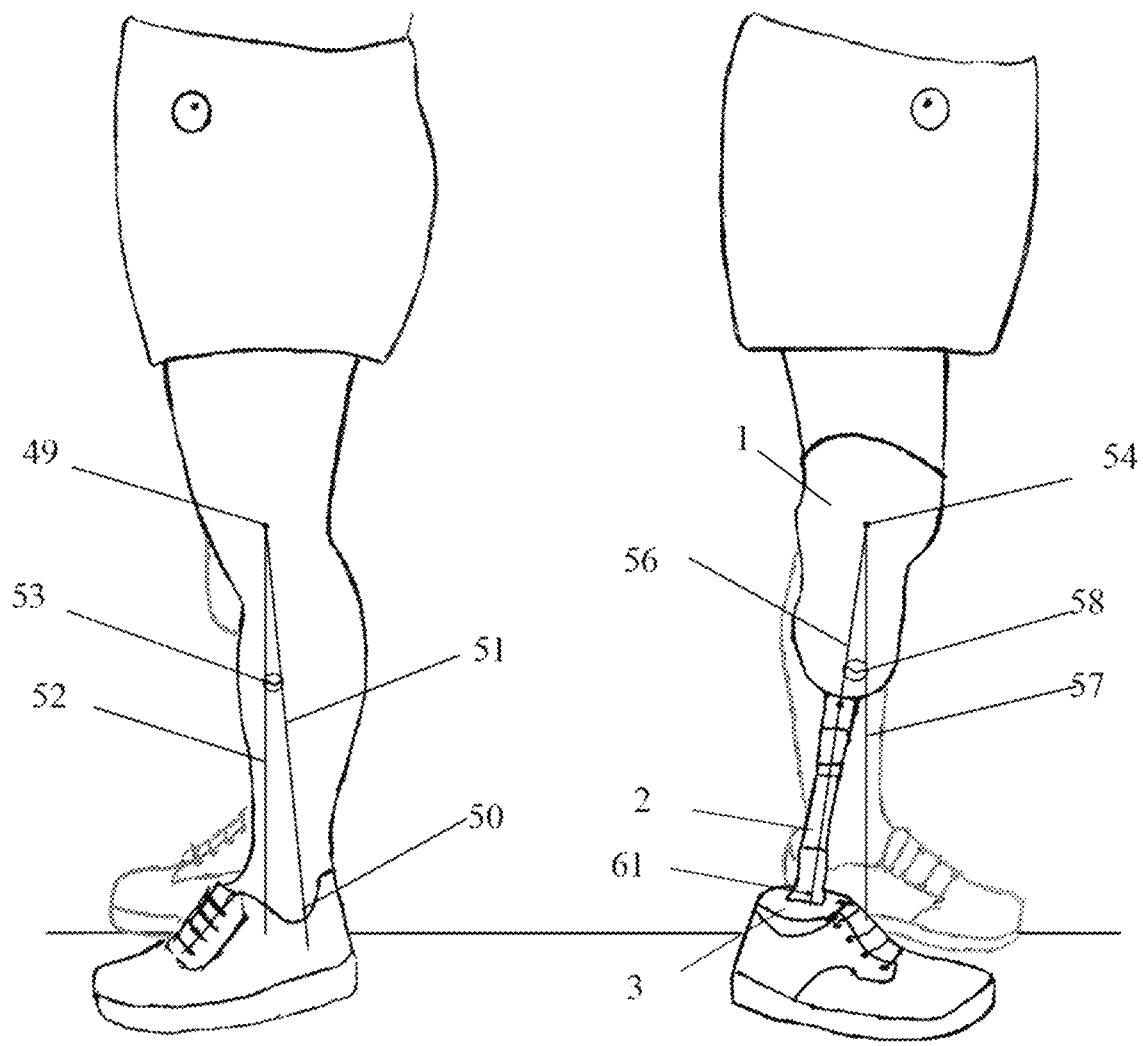
FIG. 16 depicts one or more steps in the process of determining proper alignment of the angle of the pylon of the prosthetic device in the sagittal plane.

The next step in the process of prosthetic alignment involves evaluating the angle of the pylon 2 in the sagittal plane and correcting it, if needed, as depicted in FIG. 16. This requires measuring the angle on the uninjured side, as discussed above. For this purpose, the midpoint 49 of the knee joint in the sagittal plane is identified using a long jaw caliper, while the patient is standing. Once the midpoint 49 is identified, a straight vertical beam 52 in the sagittal plane which starts at the midpoint 49 is generated. Then, an angular laser unit whose radius of radiation can be changed is used to generate a laser beam 51 which starts at the midpoint 49 and is extended to pass through the external ankle 50. The angle 53 between the two beams 52 and 51 is then measured.

A similar process is used in the amputation side to locate the midpoint 54, generate a vertical beam 57, generate a beam 56 that connects the midpoint 54 to a midpoint 61 in the sagittal plane that is located between the prosthetic foot and the pylon 2, and measure the angle 58. According to experiments performed by the inventors of the current application, best alignment results are achieved when the angle 58 is approximately equal to the angle 53. If the measured angles do not comply with these requirements, the prosthesis is removed and the angle of the socket is adjusted as needed to obtain the desired results.

Figure 17:
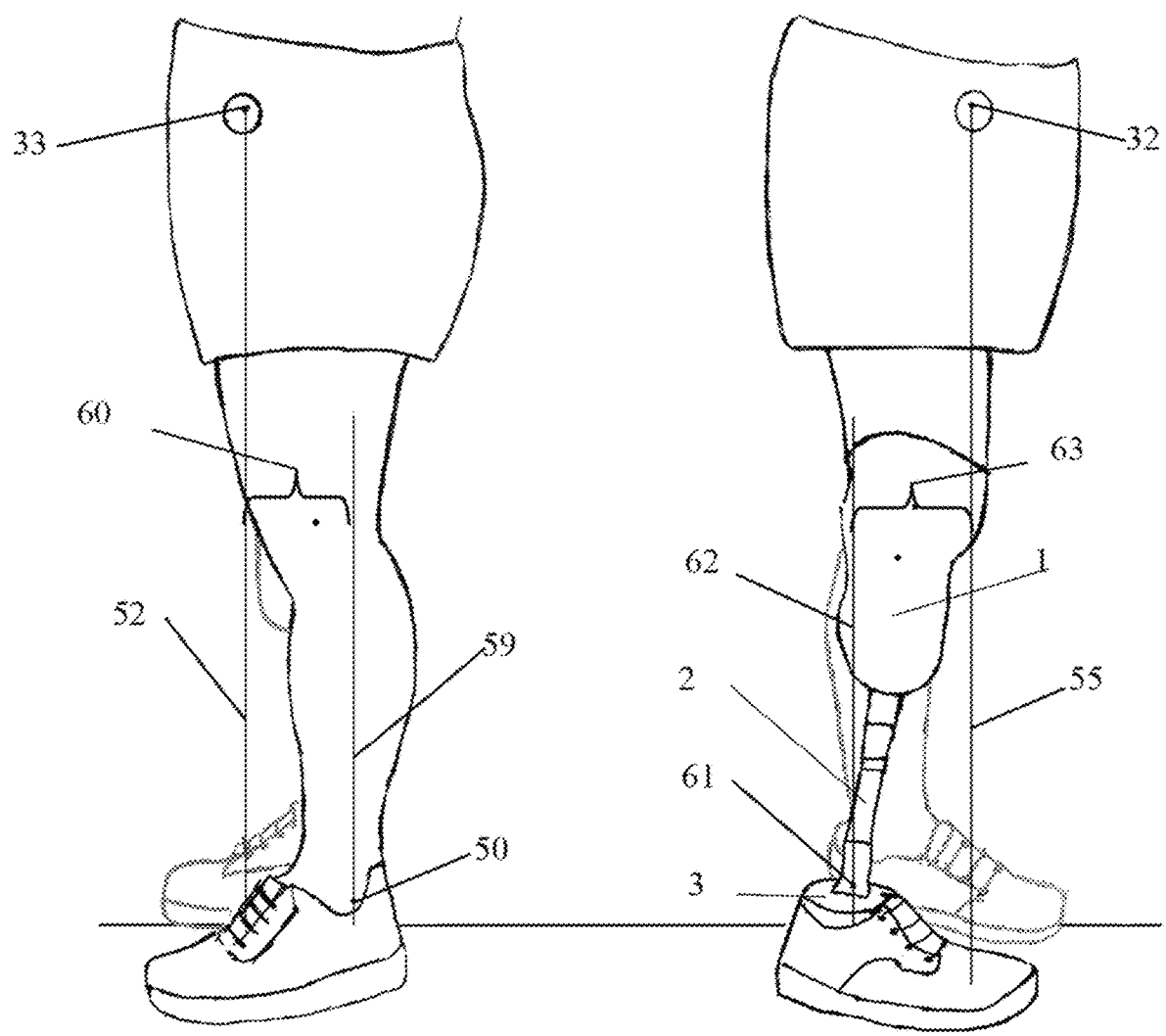
FIG. 17 depicts one or more steps in the process of determining proper alignment of the horizontal angle of the prosthetic foot in the sagittal plane.

FIG. 17 depicts making the measurements involved in performing the next step in the improved process of prosthetic alignment. This step requires making measurements and comparing the values of the distances 60 and 63. To do this, first, a straight vertical beam 52 that crosses the ASIS anatomical landmark 33 is generated by a vertical laser unit. Then, a second straight vertical beam 59 that crosses a point on the lateral malleolus 50 is generated. The distance 60 between these two vertical beams is measured using the indicator 23 of the ruler 22. At this time, a vertical beam 55 crossing the ASIS anatomical landmark 32 on the amputation side is generated using a vertical laser unit, before another vertical beam 62 that crosses the center point 61 at which the pylon 2 attaches to the prosthetic foot is also generated. The horizontal distance 63 between the vertical beams 55 and 62 is then determined using the indicator 23 of the ruler 22. The distances 63 and 60 are then compared to determine if they have the appropriate proportion with respect to each other. In one implementation, proper prosthetic alignment is identified as requiring the distance 63 to be approximately 57% larger than the distance 60. If the distance 63 does not satisfy this requirement, then the horizontal position 9 (of FIG. 2F) of the prosthetic foot in the sagittal plane is modified until the desired proportion between the distances 63 and 60 is achieved.

Figure 18:
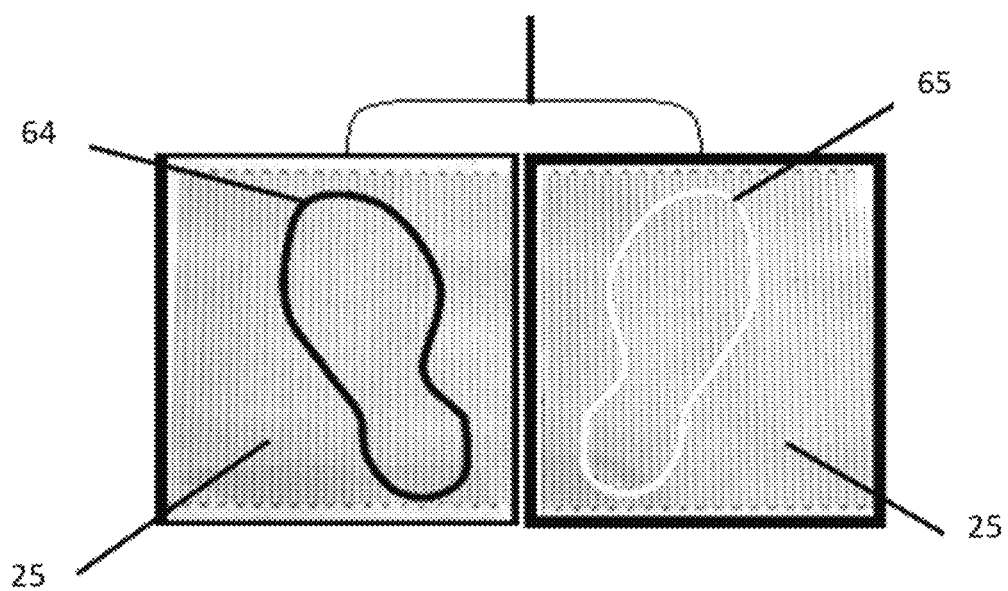
FIG. 18 depicts one or more steps in the process of determining proper alignment the prosthetic foot in the transverse plane.

According to research and experimentation done by the inventors, best alignment results are achieved when the angle of the uninjured foot and the angle of prosthetic foot on the transverse plane are approximately the same. Therefore, the next step in the improved process of prosthetic alignment involves equalizing coordinates of the uninjured foot on the transverse plate with the coordinates of the prosthetic foot on the transverse plane. This is depicted in FIG. 18. For this purpose, first, the foot prints 64 and 65 of the foot and the prosthetic foot are drawn or otherwise provided on the coordinate plates 25 of the scales 26a and 26b. Then, if a visible difference is observed in the angle of the prosthetic foot and the angle of the uninjured foot, the position 10 (of FIG. 2G) of the prosthetic foot is modified until the angles correspond with each other.

In one implementation, the weight bearing on of each of the scales 26a and 26b is also compared in making the prosthetic alignment. That is because, in one implementation, to provide clinically acceptable alignment, the weight bearing on the uninjured leg and the amputated leg should be approximately equal. The scale 26a and 26b help monitor and control possible weight shifts of the patient to either of the injured or uninjured side during the prosthetic alignment process.

Accordingly, the improved method of determining prosthetic alignment involves utilizing a system which includes multiple movable laser generating units and an integrated scale to measure angles and other variables of the uninjured leg, compare those to angles and variables of the amputated side, and make adjustments to the prosthetic device based on the comparison to ensure proper alignment. For example, the amount of tilt to the side of the prosthetic socket, the amount of tilt to the front and back of the prosthetic socket, the amount of tilt of the prosthetic foot in the sagittal plane, the displacement of the prosthetic foot in the sagittal plane, the rotation of the prosthetic foot in the transverse plane, and the height of the prosthetic device can be adjusted based on measured parameters of the uninjured leg to ensure proper alignment. The process is simple to use and does not take too much time, thereby reducing the cost and time associated with the alignment process.

The separation of various components in the examples described above should not be understood as requiring such separation in all examples, and it should be understood that the described components and systems can generally be integrated together in a single packaged into multiple systems.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations for the purpose of streamlining the disclosure. This method of disclosure is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

What is claimed is:

1. A system for aligning a prosthetic device comprising:
   a support mechanism having an adjustable height attached to a laser generating unit, the laser generating unit configured for generating a horizontal laser beam;
   a base having a three-sided frame, wherein each of the three sides houses one or more sets of rail mechanisms; and
   an integrated scale having two identical scales attached to each other;
   wherein each set of the one more sets of rail mechanism includes at least two vertical beam generating laser units and one angular laser unit whose radius of radiation can be changed, and wherein each of the two vertical beam generating laser units is attached to a measuring device having an indicator for measuring a distance the vertical laser unit travels, wherein:
   each of the laser unit, the at least two vertical laser units, and the angular laser unit whose radius of radiation can be changed, includes a laser beam diode for generating a laser line beam, and
   the height of each of the at least two vertical beam generating laser units is different from each other and from a height of the laser unit whose radius of radiation can be changed.

2. The system for aligning a prosthetic device of claim 1, wherein each of the laser generating unit, the at least two vertical beam generating laser units, and the laser unit whose radius of radiation can be changed, includes a power switch.

3. A system for aligning a prosthetic device comprising:
   a support mechanism having an adjustable height attached to a laser generating unit, the laser generating unit configured for generating a horizontal laser beam;
   a base having a three-sided frame, wherein each of the three sides houses one or more sets of rail mechanisms; and
   an integrated scale having two identical scales attached to each other, wherein:
   each set of the one more sets of rail mechanism includes at least two vertical beam generating laser units and one angular laser unit whose radius of radiation can be changed, and wherein each of the two vertical beam generating laser units is attached to a measuring device having an indicator for measuring a distance the vertical laser unit travels,
   the laser unit whose radius of radiation can be changed is attached to a member having a pointer and at least one knob, and
   the at least one knob moves a marking plate with respect to the laser unit whose radius of radiation can be changed.

4. The system for aligning a prosthetic device of claim 3, wherein moving the pointer changes an angle of a laser beam generated by the angular laser unit whose radius of radiation can be changed.

5. The system for aligning a prosthetic device of claim 1, wherein each of the two identical scales is covered by a coordinate plate.

6. The system for aligning a prosthetic device of claim 1, wherein each set of rail mechanism includes a plurality of parallel rail mechanisms.

7. A method of aligning a prosthetic device, comprising:
   determining if an adjustment of a height of the prosthetic device is needed based on a comparison of a location of an anterior superior iliac spine (ASIS) landmark on an uninjured leg side of a patient wearing the prosthetic device and a location of an ASIS landmark on an amputated side of the patient, and making the adjustment of the height, when needed;
   determining if an adjustment of an angle of a socket of the prosthetic device in the frontal plane is needed based on a comparison of an angle of a shin on the uninjured side and an angle of the socket on the amputated side, and making the adjustment of the angle of the socket, when needed;
   determining if an adjustment of an angle of a pylon of the prosthetic device in the frontal plane is needed based on a comparison of an angle of a shin on the uninjured side and an angle of the pylon on the amputated side, and making the adjustment of the angle of the pylon, when needed;

determining if an adjustment of a position of a prosthetic foot of the prosthetic device in the frontal plane is needed and making the adjustment of the position of a prosthetic foot, when needed;

determining if an adjustment of an angle of the socket in the sagittal plane is needed and making the adjustment of the angle of the socket in the sagittal plane, when needed;

determining if an adjustment of an angle of the pylon in the sagittal plane is needed and making the adjustment of the angle of the pylon in the sagittal plane, when needed;

determining if an adjustment of a horizontal position of the prosthetic foot in the sagittal plane is needed and making the adjustment of the horizontal position of the prosthetic foot in the sagittal plane, when needed; and determining if an adjustment of an angle of the prosthetic foot in a transverse plane is needed and making the adjustment of the angle of the prosthetic foot in a transverse plane, when needed.

8. The method of aligning a prosthetic device of claim 7, including generating a horizontal laser beam crossing the ASIS landmark on the uninjured leg side to compare the location of the ASIS landmark on the uninjured leg side to the location of the ASIS landmark on the amputated side.

9. The method of aligning a prosthetic device of claim 7, including generating a vertical laser beam crossing a midpoint of a knee joint and a midpoint of an ankle on the uninjured side, and generating a vertical laser beam crossing the midpoint of the knee joint in the frontal plane to measure the angle of the shin on the uninjured side.

10. The method of aligning a prosthetic device of claim 9, including generating a vertical laser beam crossing a midpoint of the socket and an end of the socket in the frontal plane on the amputated side, and generating a vertical laser beam crossing the midpoint of the socket in the frontal plane to measure the angle of the socket on the uninjured side in the frontal plane.

11. The method of aligning a prosthetic device of claim 7, including generating a vertical laser beam crossing a midpoint of a knee joint on the socket and an end of the pylon in the frontal plane on the amputated side, and generating a vertical laser beam crossing the midpoint of the knee joint in the frontal plane to measure the angle of the pylon on the amputated side in the frontal plane.

12. The method of aligning a prosthetic device of claim 7, including generating a first vertical laser beam crossing the ASIS anatomical landmark on the uninjured side, and generating a second vertical laser beam crossing the midpoint of an ankle on the uninjured side to determine a distance between the first vertical laser beam and the second vertical laser beam.

13. The method of aligning a prosthetic device of claim 12, including generating a third vertical laser beam crossing the ASIS anatomical landmark on the amputated side, and generating a forth vertical laser beam crossing the midpoint of the pylon to the prosthetic foot on the amputated side to determine a distance between the third vertical laser beam and the forth vertical laser beam.

14. The method of producing an activated carbon fabric of claim 13, further comprising comparing the distance between first vertical laser beam and the second vertical laser beam with the distance between the third vertical laser beam and the forth vertical laser beam to determine if the adjustment of the position of the prosthetic foot in the frontal plane is needed.

15. The method of aligning a prosthetic device of claim 7, further comprising: creating a footprint of a foot of the uninjured leg on a first coordinate sheet and a footprint of the prosthetic foot on a second coordinate sheet to determine if the adjustment of the position of the prosthetic foot in the transverse plane is needed.

16. The method of aligning a prosthetic device of claim 7, including generating a vertical laser beam crossing a midpoint of a knee joint on the uninjured side and generating a laser beam crossing the midpoint and a lateral malleolus of the uninjured side to measure an angle of the shin in the sagittal plane.

17. The method of aligning a prosthetic device of claim 16, including generating a vertical laser beam crossing a midpoint of the socket on the amputation side in the sagittal plane, generating a laser beam crossing the midpoint of the socket and a point located in between the socket and a pylon to measure an angle of the socket in the sagittal plane, comparing the angle of the shin and the angle of the socket to determining if an adjustment of the angle of the socket in the sagittal plane is needed.

* * * * *